US012612437B2

(12) United States Patent  (10) Patent No.:  US 12,612,437 B2
Mcconville et al.  (45) Date of Patent:  Apr. 28, 2026

(54) ZEIN-ENRICHED AND DEPLETED PROTEIN

(71) Applicant: CARGILL, INCORPORATED, Wayzata, MN (US)

(72) Inventors: Erika Lyn Mcconville, Minneapolis, MN (US); Michael A. Porter, Maple Grove, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 102 days.

(21) Appl. No.: 16/649,125

(22) PCT Filed: Sep. 21, 2018

(86) PCT No.: PCT/US2018/052153

§ 371 (c)(1),
(2) Date: Mar. 19, 2020

(87) PCT Pub. No.: WO2019/060673

PCT Pub. Date: Mar. 28, 2019

(65) Prior Publication Data

US 2021/0147493 A1 May 20, 2021

Related U.S. Application Data

(60) Provisional application No. 62/561,931, filed on Sep. 22, 2017.

(51) Int. Cl.
| | |
|---|---|
| *C07K 14/425* | (2006.01) |
| *A23J 1/12* | (2006.01) |
| *A23L 7/10* | (2016.01) |

(52) U.S. Cl.
CPC .............. *C07K 14/425* (2013.01); *A23J 1/12* (2013.01); *A23L 7/198* (2016.08); *A23V 2002/00* (2013.01)

(58) Field of Classification Search
CPC . A23L 7/198; A23L 33/185; A23J 1/12; A23J 3/14; C07K 14/42; C07K 14/425; A23V 2002/00; A23V 2000/00
USPC ........................................................ 426/656
See application file for complete search history.

(56) References Cited

U.S. PATENT DOCUMENTS

| | | | |
|---|---|---|---|
| 2,105,760 | A | 1/1938 | Swallen |
| 2,120,946 | A | 6/1938 | Swallen |
| 2,124,284 | A | 7/1938 | Bole |
| 2,133,591 | A | 10/1938 | Swallen |
| 2,156,928 | A | 5/1939 | Swallen |
| 2,218,221 | A | 10/1940 | Schopmeyer |
| 2,227,605 | A | 1/1941 | Swallen |
| 2,360,381 | A | 10/1944 | Walsh |
| 2,384,388 | A | 9/1945 | Monte |
| 2,414,195 | A | 1/1947 | Evans |
| 2,704,257 | A | 3/1955 | De Sollano |

| | | | |
|---|---|---|---|
| 4,018,936 | A | 4/1977 | Garbutt et al. |
| 4,024,120 | A | 5/1977 | Phillips |
| 4,108,847 | A | 8/1978 | Creinin |
| 4,213,941 | A | 7/1980 | Boomer |
| 4,265,925 | A | 5/1981 | Campbell |
| 4,361,651 | A | 11/1982 | Keim |
| 4,624,805 | A | 11/1986 | Lawhon |
| 4,716,218 | A | 12/1987 | Chen |
| 5,254,673 | A | * 10/1993 | Cook ........................ A23J 3/18 |
| | | | 530/424 |
| 5,254,763 | A | 10/1993 | Gill |
| 5,367,055 | A | 11/1994 | Takahashi |
| 5,410,021 | A | 4/1995 | Kampen |
| 5,498,431 | A | 3/1996 | Lindner |
| 5,510,463 | A | 4/1996 | Takahashi |
| 5,580,959 | A | 12/1996 | Cook |
| 5,602,286 | A | 2/1997 | Muralidhara |
| 5,798,446 | A | 8/1998 | Neumuller |
| 5,847,238 | A | 12/1998 | Muralidhara |
| 6,169,217 | B1 | 1/2001 | Cheryan |
| 6,433,146 | B1 | 8/2002 | Cheryan |
| 6,602,985 | B1 | 8/2003 | McInnis |
| 6,610,831 | B1 | 8/2003 | McInnis |
| 6,846,909 | B2 | 1/2005 | Mairal |
| 7,045,607 | B2 | 5/2006 | Cheryan |
| 7,829,680 | B1 | 11/2010 | Sander |

(Continued)

FOREIGN PATENT DOCUMENTS

| | | |
|---|---|---|
| CN | 1899076 A | 1/2007 |
| CN | 101560252 A | 10/2009 |

(Continued)

OTHER PUBLICATIONS

NPL Mao et al. (in Int. J Mol. Sci. 15, 2003-2014, 2014). (Year: 2014).*
NPL Nielsen et al. (in Cereal Chemistry, vol. 47 (5): pp. 501-512, 1970) (Year: 1970).*
NPL El-Hawwary et al. (in Agric. Res. Review 67 (4): 611-618, 1989) (Year: 1989).*
Google search report for NPL Mao et al. (p. 3 second reference) [Retrieved on Apr. 15, 2022]. (Year: 2022).*
Google search report for NPL Nielsen et al. (p. 1 , first referemce) [retrieved on Apr. 22, 2022].] (Year: 2022).*
Google search report retrieved for NPL El-Hawwary et al. (p. 1 second reference) [Retrieved on Apr. 15, 2022]. (Year: 2022) (Year: 2022).*

(Continued)

*Primary Examiner* — Erik Kashnikow
*Assistant Examiner* — Bhaskar Mukhopadhyay

(57) ABSTRACT

Described herein is a corn protein product, comprising a first fraction comprising 75 wt % to 95 wt % (dry solids) protein and a second fraction comprising 60 wt % to 80 wt % (dry solids) protein, wherein the first fraction is a zein-enriched fraction and the second fraction is a zein-depleted fraction and a method of achieving the same. Further described herein is a corn protein product derived from destarched corn gluten meal comprising a first fraction comprising 78 wt % to 83 wt % (dry solids) protein and a second fraction comprising 70 wt % to 80 wt % (dry solids) protein, wherein the first fraction is a zein-enriched fraction and the second fraction is a zein-depleted fraction.

15 Claims, 4 Drawing Sheets

(56) References Cited

U.S. PATENT DOCUMENTS

| | | | |
|---|---|---|---|
| 8,795,760 | B2 | 8/2014 | Lawton, Jr. |
| 9,226,515 | B2 | 1/2016 | Slabbekoorn |
| 2001/0009040 | A1 | 7/2001 | Duvick |
| 2002/0183490 | A1 | 12/2002 | Cheryan |
| 2003/0066106 | A1 | 4/2003 | Strissel |
| 2003/0198725 | A1 | 10/2003 | Cardenas |
| 2004/0009263 | A1 | 1/2004 | Liu |
| 2005/0008759 | A1 | 1/2005 | Nie |
| 2005/0064079 | A1 | 3/2005 | Allen |
| 2005/0074538 | A1 | 4/2005 | Elder |
| 2006/0057275 | A1 | 3/2006 | Wu |
| 2006/0182857 | A1 | 8/2006 | Thorre |
| 2006/0240169 | A1 | 10/2006 | Heydtmann |
| 2007/0087101 | A1 | 4/2007 | Gusek |
| 2007/0172914 | A1* | 7/2007 | Slabbekoorn ........... A23J 1/005 |
| | | | 435/68.1 |
| 2008/0102502 | A1 | 5/2008 | Foody |
| 2008/0118626 | A1 | 5/2008 | Mcwilliams |
| 2009/0041901 | A1 | 2/2009 | Elmusa |
| 2009/0053368 | A1 | 2/2009 | Fox |
| 2009/0148589 | A1 | 6/2009 | Fox |
| 2009/0209423 | A1 | 8/2009 | Slabbekoorn |
| 2009/0215990 | A1 | 8/2009 | Cheryan |
| 2010/0016554 | A1 | 1/2010 | Cheryan |
| 2010/0159521 | A1 | 6/2010 | Cirakovic |
| 2010/0221387 | A1 | 9/2010 | Cristianini |
| 2010/0233756 | A1 | 9/2010 | Sunvold |
| 2012/0027890 | A1 | 2/2012 | Cerne |
| 2013/0273219 | A1 | 10/2013 | Baier |
| 2014/0123855 | A1 | 5/2014 | Lawton, Jr. |
| 2014/0161962 | A1 | 6/2014 | Boebel |
| 2014/0193547 | A1 | 7/2014 | Brown |
| 2014/0220217 | A1 | 8/2014 | Brown |
| 2014/0271928 | A1 | 9/2014 | Rehage |
| 2014/0303348 | A1 | 10/2014 | Lawton, Jr. |
| 2014/0343259 | A1 | 11/2014 | Bleyer |
| 2014/0356510 | A1 | 12/2014 | Schweizer |
| 2015/0201647 | A1 | 7/2015 | Fosdick |
| 2016/0165932 | A1 | 6/2016 | Armentrout |
| 2016/0286840 | A1 | 10/2016 | Shane |
| 2017/0354737 | A1 | 12/2017 | Harel |
| 2019/0029295 | A1 | 1/2019 | Mielgo Iza |
| 2020/0236977 | A1 | 7/2020 | Li |

FOREIGN PATENT DOCUMENTS

| | | | |
|---|---|---|---|
| CN | 101703146 | A | 5/2010 |
| CN | 102037134 | A | 4/2011 |
| CN | 101560252 | B | 1/2012 |
| CN | 102669406 | A | 9/2012 |
| CN | 103059116 | A | 4/2013 |
| CN | 103554278 | A | 2/2014 |
| CN | 104938763 | A | 9/2015 |
| CN | 105541982 | A | 5/2016 |
| CN | 106009766 | B | 11/2017 |
| EP | 0510537 | B1 | 7/1997 |
| EP | 0648078 | B1 | 4/2001 |
| EP | 2491794 | A1 | 8/2012 |
| EP | 2401920 | B1 | 2/2013 |
| EP | 3075259 | A1 | 10/2016 |
| EP | 3375290 | A2 | 9/2018 |
| FR | 2902607 | B1 | 6/2019 |
| JP | 5754564 | A | 4/1982 |
| JP | 63185998 | | 8/1988 |
| JP | 63185999 | | 8/1988 |
| JP | H07179334 | A | 7/1995 |
| JP | 2011097928 | A | 5/2011 |
| JP | 4750901 | B2 | 8/2011 |
| JP | 06189687 | B2 | 3/2015 |
| KR | 101409213 | B1 | 6/2014 |
| WO | 8809622 | A1 | 12/1988 |
| WO | 1991012730 | A2 | 9/1991 |
| WO | 9312667 | W | 7/1993 |
| WO | 1998044807 | A1 | 10/1998 |
| WO | 0150882 | A2 | 7/2001 |
| WO | 2005074704 | A1 | 8/2005 |
| WO | 2005091995 | A2 | 10/2005 |
| WO | 2007019227 | A1 | 2/2007 |
| WO | 2009155350 | A1 | 12/2009 |
| WO | 2014186567 | A1 | 11/2014 |
| WO | 2015004448 | A1 | 1/2015 |
| WO | 2015109276 | A1 | 7/2015 |
| WO | 2016154441 | A1 | 9/2016 |
| WO | 2017011625 | A1 | 1/2017 |
| WO | 2017040273 | A2 | 3/2017 |
| WO | 2017058501 | A1 | 4/2017 |
| WO | 2017081347 | A2 | 5/2017 |
| WO | 2017165748 | A1 | 9/2017 |
| WO | 2017165756 | A1 | 9/2017 |
| WO | 2017189322 | A1 | 11/2017 |
| WO | 2018058150 | A1 | 3/2018 |
| WO | 2018237030 | A1 | 12/2018 |
| WO | 2019028263 | A2 | 2/2019 |
| WO | 2019060179 | A1 | 3/2019 |

OTHER PUBLICATIONS

Google search report retrieved for NPL Argos et al. (p. 2 second reference) [Retrieved on Apr. 18, 2022]. (Year: 2022) (Year: 2022).*

NPL Argos et al. (in J. Biol Chem. vol. 217 (17): pp. 9984-9990, 1982). (Year: 1982).*

Inglett, GE et al. High-shear, Jet-cooking, and Alkali Treatment of Corn Distillers' Dried Grains to Obtain Products with Enhanced Protein, Oil and Phenolic Antioxidants. Food Science and Technology International, vol. 16, No. 4, Jul. 9, 2010, pp. 297-308.

Johansson, D et al., Influence of Surface lipids in Commercial Zein on Microstructure and Rheological Properties of Gluten-Free Dough, Annual Transactions of the Nordic Theology Society, vol. 20, 2012, pp. 247-251.

Shukla et al: "Zein: the industrial protein from corn", Industrial Crops and Products, Elsevier, NL, vol. 13, No. 3, Jan. 1, 2001 (Jan. 1, 2001), pp. 171-192, XP002459554, ISSN: 0926-6690, DOI: 10.1016/S0926-6690(00)00064-9.

Wu, Y et al., Balancing of sulfur storage in maize seed. BMC Plant Biology, vol. 12, May 30, 2012, 77.

Wu, YV et al., Protein-Rich Residue from Corn Alcohol Distillation; Fractionation andchemistry, vol. 58, No. 4, Apr. 1981, pp. 343-347.

"The Corn Refining Process" 2 pages, downloaded from https://corn.org/wp-contentiuploads/2009/11/CornRefiningProcess.pdf (Year: 2009).

(International Standard ISO) Native starch—Determination of starch content—Ewers polarimetric method. ISO 10520. Sep. 1997.

(Solvay Interox) "Hydrogen Peroxide Controlling reduced sulphur compounds" Mar. 2011; [retrieved May 25, 2017]. Retrieved from the Internet: <URL:http://www.solvay.com/au/en/binaries/Controlling%20reduced%20suphur%20species-202502.pdf>.

Anderson, "Detoxification of Aflatoxin-Contaminated Corn", Proc. Symp. held in Atlanta, Ga., Jan. 26-27, 1982. Soth. Coop. Ser. Bull. 279:87-90 (Year: 1982).

Anderson, R. A.; "Detoxification of Aflatoxin-Contaminated Corn", Cereal Chemistry, 55, 87-90, Jan. 31, 1978.

Anderson, Timothy J., et al., "Development of New Method for Extraction of a-Zein from Corn Gluten Meal Using Different Solvents", Cereal Chem. 88(4): 356-362, 2011.

Anderson, Timothy J., et al., "Zein Extraction from Corn, Corn Products, and Coproducts and Modifications for Various Applications: A Review", Cereal Chem. 88(2): 159-173, 2011.

Anderson, Timothy James, "Extraction of zein from corn co-products", Master thesis, 2011, Food Science and Technology, Iowa State University, pp. i-v and 1-114.

Anonymous: "Establishing Instrumental color difference tolerances for your products", Jan. 1, 2008 (Jan. 1, 2008), pp. 1-17, XP093085388, Retrieved from the Internet: URL:https://support.hunterlab.com/hc/en-us/article_attachments/201371449 [retrieved on Sep. 25, 2023].

Bookwalter Corn Distillers Grains and Other By-Products of Alcohol Production in Blended Foods. II. Sensory, Stability, and Processing Studies, Cereal Chem. vol. 61, No. 6, 1984, 509-513.

(56) References Cited

OTHER PUBLICATIONS

Bryla, Marcin, et al., "Effects of pH and Temperature on the Stability of Fumonisins in Maize Products", Toxins 2017, 9, 88; doi:10.3390/toxins9030088.

Burns TD et al: Fumonisin concentrations and in vivo toxicity of nixtamalized Fusarium verticillioides culture material: Evidence for fumonisin-matrix interactions, Food and Chemical Toxicology, Pergamon, GB, vol. 46, No. 8, Aug. 1, 2008 (Aug. 1, 2008) , pp. 2841-2848, XP022939030, ISSN: 0278-6915, DOI: 10.1016/J.FCT. 2008.05.017 [retrieved on May 29, 2008].

Cielab color space—Wikipedia; https://en.wikipedia.org/wiki/CIELAB_color_space; retrieved Oct. 5, 2019; 9 pages.

Database WPI, Week 198219, Thomson Scientific, London, GB; AN 1982-38049E, XP002794657, & JPS5754564A (Nippon Shokuhin Kako KK), Apr. 1, 1982 (Apr. 1, 1982).

Dickey, L.C., "Ethanolic Extraction of Zein from Maize", Industrial Crops and Products 13 (2001), Apr. 30, 2000, 67-76.

Dougls, "What is the difference betwen corn meal& corn gluten meal?", published Jul. 8, 2011, web link: https://healthfully.com/302484-what-is-the-difference-between-corn-meal-corn-gluten-meal.html (Year: 2011).

Gomez, M.H., et al., "Changes in the Starch Fraction During Extrusion-cooking of Corn", Food Science, vol. 48, Issue 2 (Mar. 1983); pp. 378-381, XP055512137.

Gupta Ho et al: "Plant Foods for Human Nutrition 52: Processing of maize germ oil cake into edible food grade meal and evaluation of its protein quality", Plant Foods for Human Nutrition, vol. 52, Mar. 1, 1998 (Mar. 1, 1998), pp. 1-8, XP055808466, Retrieved from the Internet: URL:https://link.springer.com/content/pdf/10.1023/A:1008088822395.pdf>.

Hojilla-Evangelista M P et al, "Sequential Extraction Processing of High-Oil Corn", Cereal Chemistry, AACC International Inc, US, (Nov. 1, 2003), vol. 80, No. 6, ISSN 0009-0352, pp. 679-683, XP001185001.

Hojilla-Evangelista Met al: "Optimizing extraction of zein and glutelin-rich fraction during sequential extraction processing of corn", Cereal Chemistry, AACC International Inc, us, vol. 80, No. 4, Jan. 1, 1979 (Jan. 1, 1979), pp. 481-484, XP009092386, ISSN: 0009-0352, DOI: 10.1094/CCHEM.2003.80.4.481.

Hojilla-Evangelista MP et al: "Characterization of Protein Extracted From Flaked, Defatted, Whole Corn by the Sequential Extraction Process!", Journal of the American Oil Chemists Society, Springer, DE, vol. 69, No. 3, Mar. 1, 1992 (Mar. 1, 1992), pp. 199-204, XP000245384, ISSN: 0003-021X, DOI: 10.1007/BF02635886.

Ho-Soo Lim et al, "Comparison of four different methods for the determination of sulfites in foods marketed in South Korea", Food Additives & Contaminants: Part A, (Jan. 16, 2014), vol. 31, No. 2, doi:10.1080/19440049.2013.857048, ISSN 1944-0049, pp. 187-196, XP055627607.

Ivanova et al. "Producing of Feed protein concentrates as a method for rational utilization of recyclable fish materials" Food processing Industry Issue 12 2011 abstract.

Johnson et al., "Optimizing Extraction of Zein and Glutelin-Rich Fraction During Sequential Extraction Processing of Corn", Cereal Chem. vol. 80, No. 4, 2003, 481-484.

L Rey et al. Drugs and Pharmaceuticals Sciences "Freezing Drying Lyophilization of Pharmaceutical and Biological Products" Chap 1 2004 (Year: 2004).

Lawton, JW, "Zein: A History of Processing and Use", Cereal Chemistry., (2002), vol. 79, No. 1, pp. 1-18, XP009092326.

Mary A. Dombrink-Kurtzman et al: Effect of Nixtamalization (Alkaline Cooking) on Fumonisin-Contaminated Corn for Production of Masa and Tortillas, Journal of Agricultural and Food Chemistry, vol. 48, No. 11, Nov. 1, 2000 (Nov. 1, 2000), pp. 5781-5786, XP055564817, US ISSN: 0021-8561, DOI: 10.1021/jf000529f.

McNeillie, Alastair, and Juli Bieser. "Hydrogen peroxide uses for the year 2000." Food Processing Oct. 1993: 59+. Business Insights: Global. Web. Feb. 9, 2016.

Momany, Frank A., et al., "Structural Characterizations of a Zein", Journal of Agricultural and Food Chemistry, 2006, 54, 543-547.

Parris Net al: "Extraction and Solubility Characteristics of Zein Proteins From Dry-Milled Corn", Journal of Agricultural and Food Chemistry, American Chemical Society, US, vol. 49, No. 8, Aug. 1, 2001 (Aug. 1, 2001) , pp. 3757-3760, XP001071383, ISSN: 0021-8561, DOI: 10.1021/JF0011790.

Paulson et al. (1984) Can. Inst. Food Sci. Technol. J. 17:202-208.

R. Dixon Phillips et al, "Corn Protein Concentrate: Functional and Nutritional Properties", Journal of Food Science, US, (1979), vol. 44, No. 4, doi:10.1111/j.1365-2621.1979.tb03470.x, ISSN 0022-1147, pp. 1152-1155, XP055495372.

Reiners et al., "Corn Proteins: Potential for their Industrial Use" 58th Annual American Association of Cereal Chemists, 1973.

Ren Ting-ting, et al., "Research on extraction of zein and its functional properties and application", Science and Technology of Cereals, Oils and Foods. vol. 22. Issue 3, May 21, 2014.

Selling et al: "The effect of extrusion processing on Zein", Polymer Degradation and Stability, Bark I NG, GB, vol. 95, No. 12, Dec. 1, 2010 (Dec. 1, 2010), pp. 2241-2249, XP027527379, ISSN: 0141-3910.

Sessa, David J., et al., "Improved Methods for Decolorizing Corn Zein", Industrial Crops and Products 18 (2003), 55-65.

Sydenham etal. J. Agric. Food Chem. 1995, vol. 43, pp. 1198-1201 (Year: 1995).

Takahara et al., JP4750901(B2)-English Translation, pp. 1-55 (Year: 2011).

Argos et al., "A structural model for maize zein proteins" Journal of Biological Chemistry 257(17):9984-9990, Sep. 10, 1982.

* cited by examiner

ZEIN-ENRICHED AND DEPLETED PROTEIN

CROSS-REFERENCE TO RELATED APPLICATIONS

This application is a national phase application of International Application No. PCT/US2018/052153, filed Sep. 21, 2018, which claims the benefit of U.S. Provisional Patent Application No. 62/561,931, filed Sep. 22, 2017, which is hereby incorporated by reference in its entirety.

TECHNICAL FIELD

This application relates to processes for creating zein-enriched and zein-depleted corn protein fractions.

BACKGROUND

There is a long history of process development related to isolation of zein for a variety of industrial uses. Zein isolation typically involves dissolution of the zein protein from corn gluten meal using aqueous ethanol and subsequent solvent and "contaminant" removal, where a major portion of the non-protein composition of the zein is lipid. Variations on this process have been developed, but always starting from corn gluten meal. While there are commercial zein producers, the zein is expensive and therefore typically unsuited to food use. In addition, the zein-depleted fraction does not seem to be used in foods. Thus two potentially high-protein ingredients are not available to food formulators.

SUMMARY

Described herein is a corn protein product, comprising a first fraction comprising 75 wt % to 95 wt % (dry solids) protein and a second fraction comprising 60 wt % to 80 wt % (dry solids) protein, wherein the first fraction is a zein-enriched fraction and the second fraction is a zein-depleted fraction and a method of achieving the same. Further described herein is a corn protein product derived from destarched corn gluten meal comprising a first fraction comprising 78 wt % to 83 wt % (dry solids) protein and a second fraction comprising 70 wt % to 80 wt % (dry solids) protein, wherein the first fraction is a zein-enriched fraction and the second fraction is a zein-depleted fraction.

FIGURES

FIG. 1 illustrates solids contained in the extract expressed as total dissolved solids (A) or percentage of initial solids recovered in the extract (B) from Empyreal® or corn gluten meal (CGM) at a range of EtOH concentrations. The solids contained in the extracted residue expressed as total solids (C) or percentage of the initial solids in the residue (D) from Empyreal or CGM at a range of EtOH concentrations.

DESCRIPTION

Figure 1A:
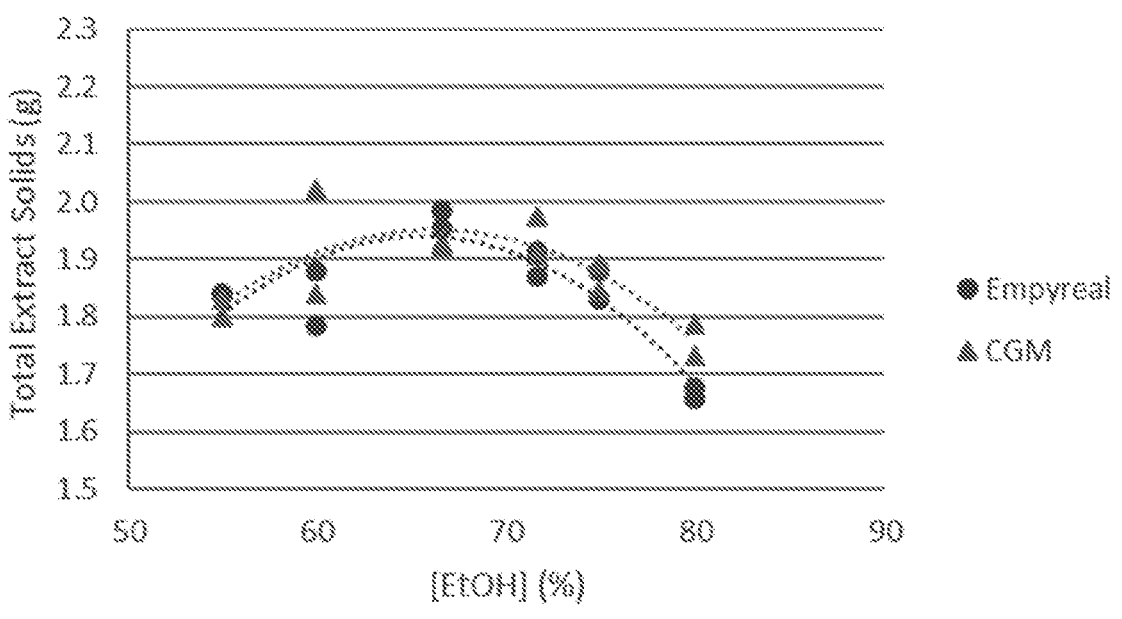

A process by which the starch in corn gluten meal is removed yielding a product with about 75% protein is disclosed in U.S. Pat. No. 9,226,515, which has been further processed to remove lipid and pigments and which has greater than 85% protein as disclosed in International Application No. PCT/2016/024020. In this process, the objective is to maximize protein yield, so conditions that minimize protein solubilization are identified and employed. The process described is also quite cost-effective.

Aspects of the invention described herein explore whether using high-water solvents might yield a novel fractionation of the corn protein. For example, the ratio of zein dissolved to total protein might vary depending on whether corn gluten meal ("CGM") or destarched (according to U.S. Pat. No. 9,226,515 and hereinafter referred to as Empyreal®) CGM is used. Similarly, there may be other proteins that are preferentially dissolved or retained as a consequence of prior heat and enzyme treatment.

The processing history of Empyreal® creates material that responds differently to ethanol extraction than corn gluten meal. This difference impacts yield, first extract purity, as well as protein and amino acid distribution. It has been surprising that the zein-enriched protein extracted from Empyreal® is not the same as the zein-enriched material extracted from CGM.

In practical terms, there is a tension between the technical properties of a material that tends to drive towards higher purity and the economic consequences of seeking high purity. A focus and intention in this technology development is on the less pure protein with attention towards lower cost. In these terms, the benefits of using Empyreal® rather than CGM as a raw material become salient. It has been found that the extracted residue from Empyreal® is close to 70% protein on a dry basis compared to about 40% from CGM (both values rise slightly after further defatting). This has a huge impact on the value of the two protein fractions as with protein under 50%, feed is the most likely outcome. With protein over 70%, food is a more likely and valuable use.

Disclosed herein is a corn protein product comprising a zein-enriched fraction (also referred to herein as a "first fraction" and an "extract") and a zein-depleted fraction (also referred to herein as a "second fraction" and a "residue"). Surprisingly herein, the zein-enriched fraction comprises 75 wt % to 95 wt % (dry solids) protein and the zein-depleted fraction comprises 60 wt % to 80 wt % (dry solids) protein. Further, in some aspects the zein-enriched fraction comprises 78 wt % to 83 wt % (dry solids) protein and the zein-depleted fraction comprises 70 wt % to 80 wt %. Unexpectedly, the zein-depleted fraction comprises a high enough protein content that it too (along with the zein-enriched fraction) can be used for food applications.

To achieve such a corn product, aspects of the present invention start with a destarched corn gluten meal, for example but not limited to Empyreal®. It has been found that destarched corn gluten meal, when compared to corn gluten meal, achieves a zein-depleted fraction higher in protein than corn gluten meal. Separation of the zein-enriched and zein-depleted fractions is achieved using an aqueous solution of an alcohol like ethanol or isopropanol. In preferred aspects, the organic solvent is an ethanol-water solvent comprising 55-80 wt % ethanol. Once the organic solvent is added to the destarched corn gluten meal, a series of solids-liquid separations (such as filtration or centrifugation) and homogenization techniques commonly known to one skilled in the art are carried out to recover a zein-enriched and zein-depleted fraction. Notably, higher ethanol concentrations increase the amount of protein present in the zein-depleted fraction. Furthermore, results suggest that using destarched corn gluten meal yields a purer protein in the zein-enriched fraction than corn gluten meal and the zein-depleted fraction can have up to 1.75 times higher protein concentration.

Also notable is that the zein-enriched and zein-depleted fractions have different amino acid distributions depending on whether corn gluten meal or Empyreal® is used as starting material, suggesting that the protein compositions of the fractions are not identical. Further, the zein-enriched and zein-depleted fractions have different fatty acid profiles.

Furthermore, the percent yield of protein is also interesting. In preferred aspects, the zein-enriched fraction is at least 50%, and more preferably at least 55% of the protein present in the starting material. In preferred aspects, the zein-depleted fraction is at least 30%, and more preferably at least 40% of the protein present in the starting material. It shall be recognized that there may some protein loss in the process. Furthermore, an optional defatting step improves the protein purity in the zein-depleted fraction. The zein-enriched and zein-depleted fractions are treated with organic solvents such as ethanol, hexane, and ethyl acetate to remove lipids and pigments.

EXAMPLES

Materials & Methods

The following materials and methods were used in the remaining examples.

CGM and Empyreal were collected as wet cakes at the Cargill Starch and Sweeteners corn wet mill in Blair, Nebr. Cakes were frozen, transported and stored frozen until shortly before use. The Empyreal® wet cake was treated with about 200 ppm $H_2O_2$ to oxidize free sulfite but the CGM was not.

Protein analysis was conducted using a Leco FP628 machine following the manufacturer's directions and using EDTA as a standard. Protein is calculated as 6.25×N.

For determining the solids content of raw materials, duplicate or triplicate samples were dried on a Sartorius moisture balance. For determining the solids content of final samples, approximately 1 g of cake or 10 g of extractant were weighed into tared aluminum dishes and left to dry at 80-100° C. for at least overnight under vacuum.

Example 1

This example shows that CGM and Empyreal® have different fractionation characteristics from each other and yield different proximate residue compositions. 10 g CGM of Empyreal cake is weighed into a 50 mL centrifuge tube. Extractant is prepared according to Table 1 and added to the tube.

TABLE 1

Extractant compositions and estimated solvent concentration expressed on a w/w basis.

| EtOH (g) | Intrinsic water (g) | Added water (g) | [EtOH] % |
|---|---|---|---|
| 24 | 6.2 | 0 | 80 |
| 22.5 | 6.2 | 1.5 | 75 |
| 21.5 | 6.2 | 2.5 | 72 |
| 20 | 6.2 | 4 | 67 |

TABLE 1-continued

Extractant compositions and estimated solvent concentration expressed on a w/w basis.

| EtOH (g) | Intrinsic water (g) | Added water (g) | [EtOH] % |
|---|---|---|---|
| 18 | 6.2 | 6 | 60 |
| 16.5 | 6.2 | 7.5 | 55 |

The tubes are shaken by hand and then the contents are mixed with a handheld homogenizer. The tubes are then placed in a 60° C. water bath. Tubes are shaken periodically and after 30 minutes, the tubes are centrifuged at 10000 rpm for 2 minutes. The supernatant is poured into a separate tube and an additional 10 g of extractant is added and re-homogenized. After an additional 30 minutes at 60° C., the supernatant is collected again after centrifugation at 10000 rpm. Supernatants are combined.

The cake is put into an A1 pan and weighed, then dried in a vacuum oven. The filtrates are combined and weighed. About 10 g of the filtrate is placed in a tared dish, air-dried partially and placed in a vacuum oven to dry.

Figure 1B:
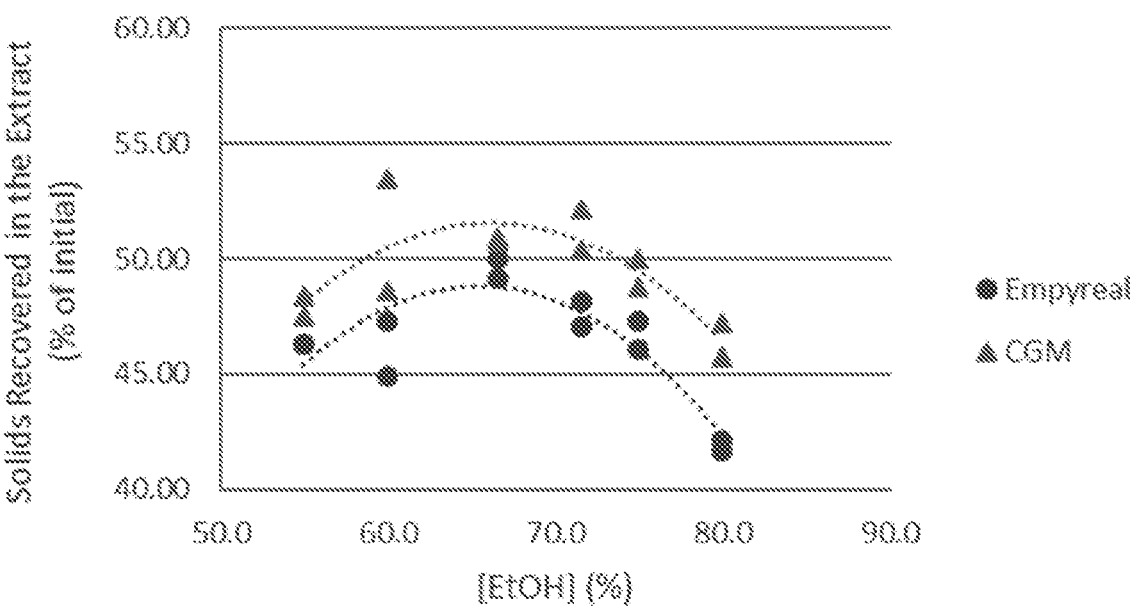

The maximum yield of extracted mass is found at about 65 wt % EtOH (FIG. 1A). The Empyreal® extract is higher solids than the CGM extract (FIG. 1B).

Figure 1C:
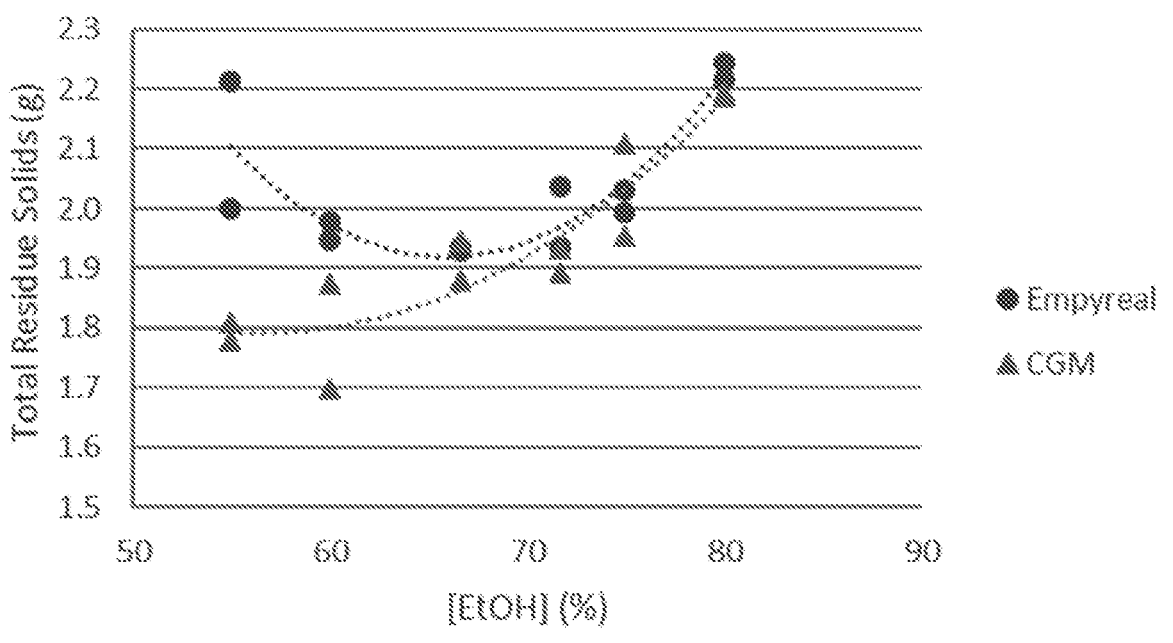
Figure 1D:
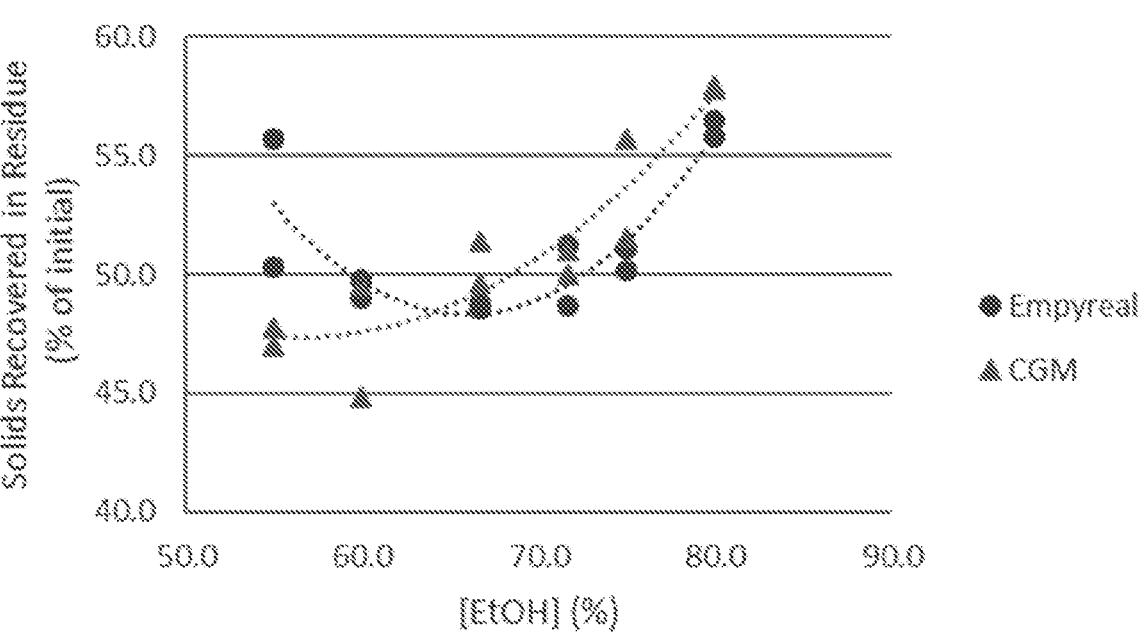

When Empyreal® is extracted, the extracted solids (residue) showed a generally inverse behavior with the minima of residual solids around 65 wt % EtOH (FIGS. 1C and 1D). With CGM, decreasing ethanol lead to lower retained solids. The same pattern is visible in the solids fraction before solvent removal.

Figure 2A:
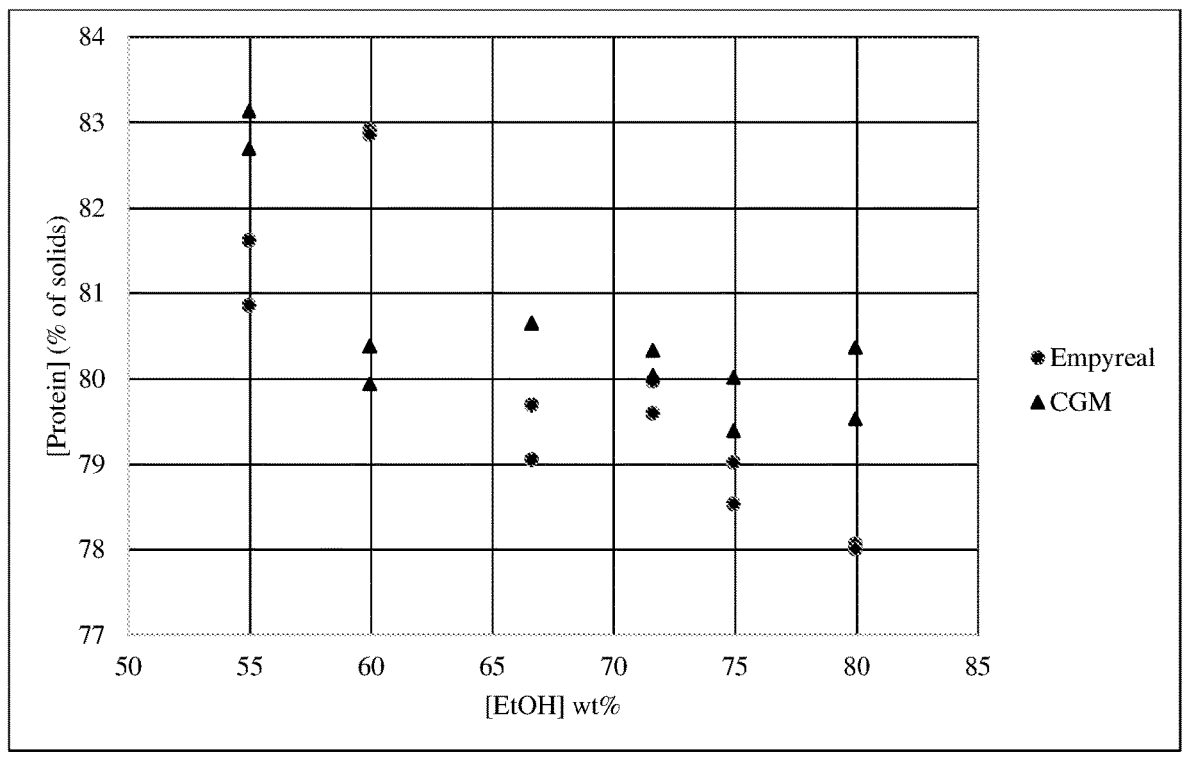
FIG. 2 illustrates protein concentrations in the solids from the extracts (A) or residue (B) as a function of starting material and ethanol concentration.
Figure 2B:
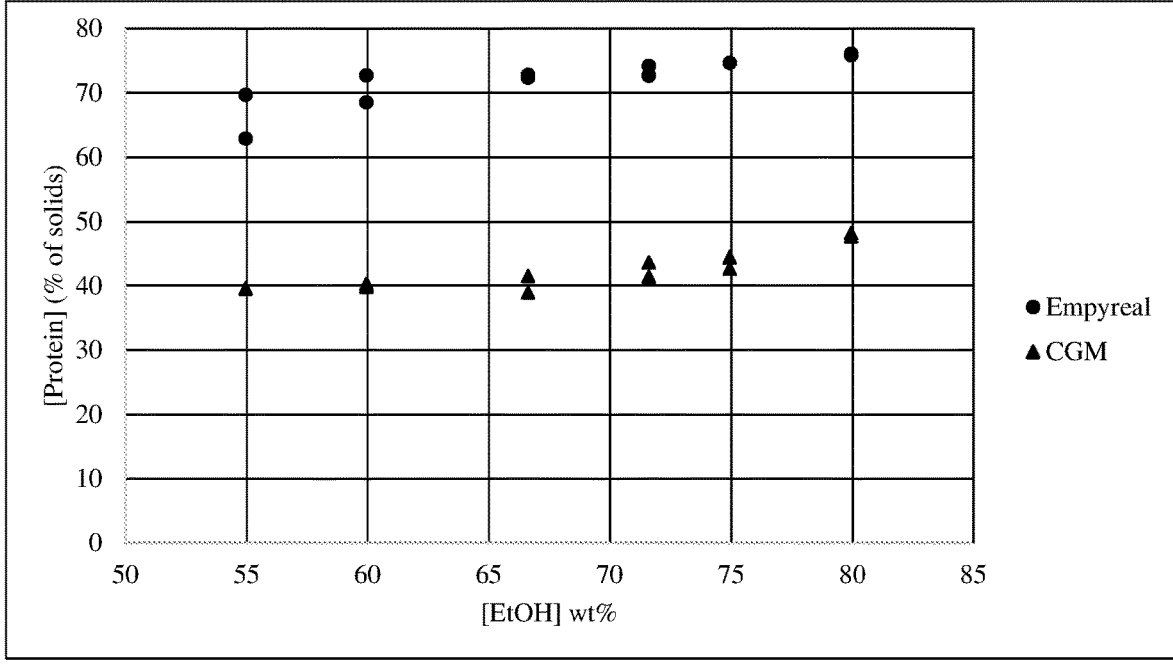

Extracts derived from Empyreal and CGM have similar concentrations of protein in their dry solids (FIG. 2A), which is the zein-enriched fraction. In contrast, the residue after extraction of Empyreal is much higher in protein than the comparable extract from CGM (FIG. 2B), which is the zein-depleted fraction. Given the higher protein concentration of Empyreal®, this observation is practically very significant. Fractionation of Empyreal® results in two fractions with greater than 70% protein on a dry basis. Fractionation of CGM results in two fractions of differing protein concentrations and thus of different utility and value.

Example 2

A representative sample of the extract and residue from a fractionation at 60° C. and 67 wt % EtOH described in Example 1 is submitted to SDS gel electrophoresis. Based on the protein concentration, samples are weighed out containing a calculated 28 mg of protein and mixed with 10 mL of 0.1N NaOH containing 1 wt % SDS. This is left overnight to hydrate and dissolve. An aliquot containing 100 μL of Laemmli buffer containing 1 mM dithiothreitol is added to 100 μL of the alkaline extract and exposed to a boiling water bath for 5 minutes. The sample is cooled and centrifuged at 13000 g for 5 minutes to remove particulates. A 20 μL aliquot is loaded into the wells of an AnykD™ Mini-PROTEAN® TGX™ Precast Gel and resolved on the Mini-PROTEAN® system. Gels are run until the marker dye reaches the bottom of the gel. Gels are stained with Bio-Safe™ Coomassie Brilliant Blue G-250 and destained in water.

Each of the samples (CGM and Empyreal® extracts ("zein-enriched")) are loaded 4 times to provide opportunity for quantitative assessment. Images of destained gels are created using Licor Odessey scanner using Image Studio version 2.0 software. Quantitation is done with the manual analysis in Image Studio version 2.0 software.

The extract samples produced relatively clear bands which permitted quantitative analysis. Zein forms a triplet of bands at about 25 kDa that dominates the profile. The triplet comprises about 76% of the extract from Empyreal® but about 57% of the extract from CGM. These are statistically different (p=0.003) using a 2-sample T-test.

Figure 3:
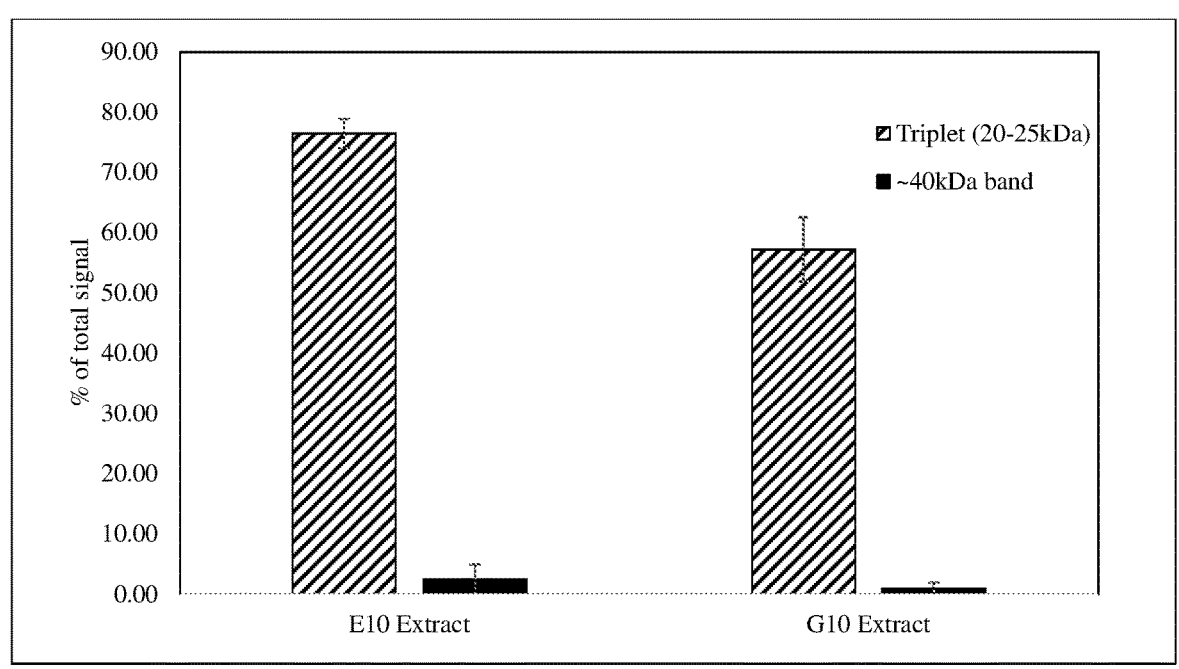
FIG. 3 illustrates quantitation of the triplet and 40 kDa bands from extracts of Empyreal (E10 extract) and CGM (G10 extract) after separation by SDS gel electrophoresis. Error bars represent the standard deviation.

A second band is also visible at about 40 kDa. This band is almost twice as prominent in the Empyreal® extract (2.48%) compared to the CGM extract (1.0%) which is also statistically different (p=0.016). This comparison is shown in FIG. 3.

Taken together, the results of Examples 1 and 2 suggest that using Empyreal® as a starting material actually yields a purer protein in the extraction than using CGM and the residual material is 1.75-times higher protein concentration. It is logical to infer that the distribution of proteins in the residue is also different as a function of the starting materials.

Example 3

The same procedure in Example 1 is used to prepare a zein-enriched extract and a zein-depleted residue from Empyreal® and CGM wet cakes. The Empyreal cake is 39.7% solids and the CGM cake is 38.9% solids. 240 g of 69 wt % EtOH is added to 100 g of thawed cake and homogenized with a hand-held homogenizer. The mixture is placed at 60° C. for 30 minutes with periodic shaking. Extract is recovered by filtration on a Buchner funnel with 18.5 cm Whatman 113 filter paper. The residue is resuspended in 250 g of 66 wt % EtOH and the extraction and filtration is repeated. The solids are resuspended a third time in 250 g of 66 wt % EtOH and the separation repeated.

The final residue is air dried. The extracts are combined and concentrated by a combination of air drying and drying under a Na stream. After sufficient solvent is removed, the protein coagulated and the solvent is poured off. The remaining mass completed air drying.

Amino acid analysis is conducted after overnight hydrolysis of samples in 6N HCl under vacuum at 110° C. After cooling, samples are neutralized with 6N KOH. The primary amino acids are derivatized in 2% diethyl ethoxymethylenemalonate in methanol solution and 1M cesium bicarbonate buffer. A 1 μL aliquot is injected onto a Waters Acquity CORTECS reversed phase C18 column (100×2.1 mm, 1.6 um) installed in an Agilent 1290 ultra-high performance liquid chromatography instrument. The derivatized amino acids are eluted by a linear gradient comprising 95% mobile phase A (20 mM ammonium formate with 0.1% formic acid) to 95% mobile phase B (acetonitrile). The analytes are then detected by UV absorbance at 282 nm. Peaks are quantified by comparison to a standard obtained from Sigma (A9781) Amino acid analyses are reported as the percent of each amino acid as a fraction of all amino acids detected.

Two comparisons are of primary interest. Table 2 shows that the amino acid distribution in the extract from Empyreal® was dissimilar to that of the extract derived from CGM.

TABLE 2

Amino acid distribution of 65 wt % EtOH extract solids from Empyreal ® and CGM. Results are expressed as a percentage of recovered amino acids plus ammonium. The Empyreal ®/Gluten ratio is shown in the right most column.

| | CGM | Empyreal | Empyreal ®/Gluten |
|---|---|---|---|
| Alanine % | 8.87 | 9.00 | 1.01 |
| Ammonium Chloride % | 10.97 | 9.55 | 0.87 |
| Arginine % | 2.64 | 2.30 | 0.87 |
| Aspartic Acid % | 4.74 | 5.23 | 1.10 |
| Glutamic Acid % | 0.58 | 0.40 | 1.00 |
| Glycine % | 24.55 | 24.43 | 0.77 |
| Histidine % | 1.50 | 1.17 | 1.05 |
| Isoleucine % | 1.15 | 1.20 | 1.11 |
| Leucine % | 3.39 | 3.76 | 1.02 |
| Lysine % | 18.77 | 19.17 | 1.51 |
| Phenylalanine % | 0.05 | 0.07 | 1.05 |
| Serine % | 5.31 | 5.51 | 1.04 |
| Threonine % | 6.60 | 6.94 | 1.03 |
| Tyrosine % | 5.31 | 5.51 | 1.01 |
| Valine % | 2.60 | 2.68 | 1.08 |

The compositions of the two extracts is compared by dividing the Empyreal®-derived amino acid concentration by the CGM-derived concentration for each amino acid. Empyreal® extract protein is relatively low in ammonia (derived from glutamine and asparagine), and glycine. Empyreal®-derived extract is enriched in aspartic acid, isoleucine and especially lysine.

TABLE 3

Amino acid distribution of 65 wt % EtOH residue solids from Empyreal and CGM. Results are expressed as a percentage of recovered amino acids plus ammonium. The Empyreal/Gluten ratio is shown in the right most column.

| | CGM | Empyreal | Empyreal/Gluten |
|---|---|---|---|
| Alanine % | 7.19 | 7.71 | 1.07 |
| Ammonium Chloride % | 7.30 | 6.12 | 0.84 |
| Arginine % | 7.12 | 6.14 | 0.86 |
| Aspartic Acid % | 7.72 | 6.52 | 0.84 |
| Glutamic Acid % | 17.84 | 19.74 | 1.11 |
| Glycine % | 5.05 | 4.52 | 0.90 |
| Histidine % | 2.85 | 2.56 | 0.90 |
| Isoleucine % | 3.76 | 3.52 | 0.94 |
| Leucine % | 10.87 | 12.83 | 1.18 |
| Lysine % | 4.78 | 3.34 | 0.70 |
| Phenylalanine % | 4.87 | 5.37 | 1.10 |
| Serine % | 5.21 | 5.29 | 1.02 |
| Threonine % | 4.39 | 4.10 | 0.93 |
| Tyrosine % | 4.72 | 5.58 | 1.18 |
| Valine % | 5.50 | 4.94 | 0.90 |

A similar analysis of the residue after extraction (Table 3) shows that Empyreal® residue is relatively depleted in ammonium, arginine, aspartic acid, glycine, histidine, lysine, and valine.

Notably, the residue comprises greater than 11.5% leucine, greater than 5.0% tyrosine, and less than 4.0% lysine on a protein basis The Empyreal®-derived fraction is enriched in glutamic acid, leucine and tyrosine Without being bound to any particular theory, the consequences of the differing amino acid compositions is not obvious, but it strongly suggests that the protein compositions of the fractions are not identical. Identical protein compositions would have identical amino acid compositions. Shifting proportions of a set of proteins could lead to shifting amino acid distributions. The results of the SDS gel electrophoresis do suggest a changing proportion of constituent proteins. The amino acid analyses are consistent with that observation.

Example 4

A 250 g sample of thawed Empyreal® cake (62.77% moisture) is placed in a 1000 mL bottle. Ethanol (424 g) and water (70 g) are added to the bottle and the mixture is homogenized with a handheld homogenizer. The bottle is placed in a 60° C. water bath and agitated periodically over a 30 minute period. The solids are recovered by filtration of the mixture through a sheet of 18.5 cm Whatman 113 filter paper. The filter cake is resuspended in 300 g of 66 wt % EtOH and returned to the water bath for 30 min with periodic shaking. The filter cake is partially collected on filter paper as before. Filtration is poor, so unfiltered suspension is centrifuged at 6000 rpm (approx. 5500 g) for 3 minutes. The pellet is combined with the filter cake and resuspended in 300 g of 66 wt % EtOH. The bottle is returned to the water bath for 30 minutes with periodic shaking. Solids are recovered by centrifugation as before. The solids are resuspended and the entire process repeated like the previous step.

The solids are recovered from the centrifuge bottles and broken into small pieces which are placed in an aluminum tray to dry under partial vacuum under warm conditions. The filtrates and supernatants are combined and concentrated by rotary evaporation at 50° C. and 24 in vacuum. When sufficient EtOH is removed, the protein agglomerates and evaporation is stopped. The protein settles and a water-rich fluid is poured off of the jelly-like mass. The soft mass is placed in an aluminum tray and dried under vacuum under warm conditions. The dried extract solids comprises about 93 wt % protein and the dried residue solids comprises about 79 wt % protein, both on a dry basis.

Samples of zein-enriched extract solids and zein-depleted residue solids are defatted by serial extractions with organic solvents: absolute ethanol, hexane, and ethyl acetate. One gram samples of dry ground extract and residue are placed in 15 mL plastic centrifuge tubes. To each tube, 3 mL of solvent is added and mixed. Samples are incubated for 10 minutes with constant inversion at room temperature. The solvent is recovered by centrifuging the samples for 3 minutes at 2000 g and then lifting off the free liquid with a pipette. The extraction is repeated 3 additional times for a total of 4 extractions. Samples are dried under a Na stream overnight. The lipid content of the fractions are measured using AOCS Ce-1h-05.

The lipid contents of fractions in this example are shown in Table 4.

TABLE 4

Comparison of lipid content before and after extraction with defatting solvents.
Results are expressed on a percent "as is" fatty acid basis in upper section.

| Extractant | Extract protein | Residue Protein | Extract protein | Residue Protein | Extract protein | Residue Protein | Extract protein | Residue Protein |
|---|---|---|---|---|---|---|---|---|
| | Saturated | | Monounsaturated | | Polyunsaturated | | Total | |
| None | 0.64 | 1.01 | 0.51 | 1.69 | 1.69 | 3.51 | 2.86 | 6.23 |
| EtOH | 0.39 | 0.66 | 0.30 | 1.06 | 1.00 | 2.20 | 1.71 | 3.94 |
| Hexane | 0.64 | 0.66 | 0.50 | 1.05 | 1.70 | 2.21 | 2.85 | 3.94 |
| Ethyl acetate | 0.60 | 0.62 | 0.47 | 0.99 | 1.56 | 2.06 | 2.64 | 3.69 |
| Fraction of fat removed | | | | | | | | |
| EtOH | 0.39 | 0.35 | 0.41 | 0.37 | 0.41 | 0.37 | 0.40 | 0.37 |
| Hexane | 0.00 | 0.35 | 0.02 | 0.38 | −0.01 | 0.37 | 0.00 | 0.37 |
| Ethyl acetate | 0.06 | 0.39 | 0.08 | 0.41 | 0.08 | 0.41 | 0.08 | 0.41 |

The residue sample has much higher total fat, and each subtype of fat concentration than the extract. Without being bound to any particular theory, this probably reflects the poor lipid dissolving power of the aqueous EtOH containing 35 wt % water. Further extraction with solvents containing minimal water decreased the total fatty acid concentration further. The results also indicate that not all solvents are equally effective in removing the lipids present in these two protein fractions.

Example 5

The bulk zein-depleted sample was defatted by first grinding the protein in a coffee grinder until the entire sample passed through a 425 μm screen. 25 g material and 125 g absolute ethanol were weighed into five, 250 mL polyethylene bottles. Bottles were hand shaken and placed in a water bath set to 40° C. The bottles were periodically hand shaken throughout the 30 minute heating period and, when removed from the water bath, centrifuged at 9000 rpm for 5 minutes. The supernatant was poured off and 75 g ethanol added to each bottle containing the remaining solids. Solids were re-suspended by hand shaking and the heating and centrifuging was repeated. The first and second defatting extractions were time consuming and inefficient so it was decided that the samples should be filtered instead of centrifuged. The third and fourth defatting extractions were conducted by adding 50 g absolute ethanol to the remaining solids, shaking, and heating in the water bath as above. After 30 minutes, the bottles were shaken to re-suspend the material and filtered using a Buchner funnel and Whatman 1 filter paper. Solids were transferred to an aluminum pan and dried in a vacuum oven set to 40° C. overnight. Results of fat content are determined using the AOCS Ce-1h-05 method To obtain the defatted zein-enriched samples, it shall be understood that additional agitation is required. Results are shown in Table 5.

TABLE 5

| Sample | Saturated Fat (wt %) db | Monoun- saturated Fat (wt %) db | Polyun- saturated Fat (wt %) db | Total Fat (wt %) db |
|---|---|---|---|---|
| Zein-Depleted Initial | 0.95 | 1.60 | 3.15 | 5.71 |
| Zein-Depleted Defatted | 0.27 | 0.37 | 0.70 | 1.35 |
| Zein-Enriched Initial | 0.53 | 0.39 | 1.28 | 2.30 |
| Zein-Enriched Defatted | 0.05 | 0.01 | 0.01 | 0.09 |

In this example, the defatted zein-depleted fraction demonstrates total fat content less than 1.5 wt % (db).

Example 6

One hundred grams of corn protein isolate (note that corn protein isolate is used because its fractionation is similar to that of Empyreal® and to illustrate defatting prior to fractionation) prepared according to PCT/US2016/024020 is placed in a 1 L plastic bottle. The loss on drying is 7.57% and the protein is 88.4% on a dry basis. Aqueous ethanol (65 wt %) is added and the suspension is homogenized then placed at 50° C. with periodic mixing for 75 minutes. Solids are collected by filtration on VWR 417 paper on a Buchner funnel. The solids are resuspended in 400 g of 65 wt %

EtOH and the incubation at 50° C. continued for 30 minutes. The solids are collected again as described above, and resuspended in 400 g of 65 wt % EtOH for 30 minutes at 50° C. The solids are collected as described above and placed in an aluminum pan to dry in an oven; this represents the residue. The filtrates are combined and held at room temperature until concentration began. The combined filtrates are concentrated in a rotary evaporator to remove about half the solvent. The concentrate is stored at about 4° C. for three days during which time a soft precipitate forms. The pellet is collected by centrifugation (3000 g, 5 minutes, ambient temperature). Further concentration did not precipitate more material and the liquid is evaporated to yield a solid material. Protein and loss on drying is analyzed for the recovered extract and residue fractions. About 15.5% of the initial protein is unaccounted for. About 45% of the protein recovered was in the extract. Table 6 shows the results.

TABLE 6

Division of protein into extract and residue from corn protein isolate and 65 wt % aqueous EtOH at 50° C.

| | Solids (g) | Protein (g) | % of initial protein |
|---|---|---|---|
| Initial | 92.4 | 81.7 | |
| Extract | 45.5 | 36.8 | 45.1 |
| Residue | 29.8 | 32.2 | 39.4 |

Example 7

Four hundred grams of corn protein isolate is prepared according to PCT PCT/US2016/024020, but collected before solvent removal, is placed in a 1 L plastic bottle. The loss on drying is 75% and the protein is 84.3% on a dry basis. The solvent composition at this point is between 98 and 100 wt % EtOH. Deionized water (161 g) is added and the suspension is homogenized then placed at 50° C. with periodic mixing for 30 minutes. Solids are collected by filtration on Whatman 113 paper on a Buchner funnel. The solids are resuspended in 260 g absolute EtOH plus 140 g of deionized water and the incubation at 50° C. continued for 30 minutes. The solids are collected again as described above, and resuspended in 260 g absolute EtOH plus 140 g of deionized water for 30 minutes at 50° C. The solids are collected as described above and suspended briefly in absolute EtOH before a final filtration and solids recovery.

The solids are placed in an aluminum pan to dry in an oven. This represents the residue of extraction. The filtrates are combined and held at room temperature until concentration begins. The combined filtrates are concentrated in a rotary evaporator to remove about two-thirds the solvent. The concentrate is stored at about 4° C. for five days during which time a soft precipitate forms. The pellet is collected by filtration as described above. Protein and loss on drying is analyzed for the recovered extract and residue fractions. About 57% of the protein recovered is in the extract. An indication of the variability in these analyses is shown by the fact that the total recovered protein exceeds the initial protein. Table 7 shows the results.

TABLE 7

Division of protein into extract and residue from pre-desolventized corn protein isolate and 65 wt % aqueous EtOH at 50° C.

|  | Solids (g) | Protein (g) | % of initial protein |
|---|---|---|---|
| Initial | 100 | 84.3 | |
| Extract | 50.8 | 48.3 | 57.2 |
| Residue | 31.9 | 37.0 | 43.8 |

Example 8

A 10 g sample of wet destarched corn gluten meal cake is weighed into a 50 mL centrifuge tube. NaOH (0.11 g of 1M solution) is added to adjust the pH to approximately 6.0. Twenty-four grams of 24 g of 89 wt % EtOH extractant is prepared and added to the cake. Cake and extractant is shaken then homogenized using a handheld mixer and placed in a 60° C. water bath with periodic mixing over 30 minutes. The suspension is centrifuged at 10000 rpm (TA10.25i rotor) for 2 minutes. The extract was decanted to a separate tube. Ten grams of 65 wt % EtOH was added to the tube, remixed and the incubation at 60° C. continued from another 15 minutes. Solids and liquids were separated by centrifugation as above. The resulting cake was placed in an aluminum pan and dried in a vacuum oven. The filtrates were combined and weighed. About 10 g of filtrate was placed in a pre-weighed dish, air-dried to remove a substantial fraction of the solvent and then dried in a vacuum oven. Loss on drying and protein concentration were determined on both. About 53% of the protein was found in the extract. Results are shown in Table 8.

TABLE 8

Division of protein into extract and residue from destarched corn gluten meal at approximately pH 6 and 65 wt % aqueous EtOH at 60° C.

|  | Solids (g) | Protein (g) | % of initial protein |
|---|---|---|---|
| Initial | 3.97 | 2.98 | |
| Extract | 1.95 | 1.58 | 53.0 |
| Residue | 1.82 | 1.40 | 47.0 |

Comparison of previous examples indicate that defatting has minimal impact on subsequent fraction of protein into the extract. Similarly, fractionation before and after solvent removal is similar.

Example 9

A 10 g sample of wet corn gluten meal cake is weighed into a 50 mL centrifuge tube. NaOH (0.326 g of 1M solution) is added to adjust the pH to approximately 6.0 similar to the pH of Empyreal®. Twenty-four grams of 24 g of 89 wt % EtOH extractant is prepared and added to the cake. Cake and extractant is shaken then homogenized using a handheld mixer and placed in a 60° C. water bath with periodic mixing over 30 minutes. The suspension is centrifuged at 10000 rpm (TA10.25i rotor) for 2 minutes. The extract is decanted to a separate tube. Ten grams of 65 wt % EtOH is added to the tube, remixed and the incubation at 60° C. continues for another 15 minutes. Solids and liquids are separated by centrifugation as above. The resulting cake is placed in an aluminum pan and dried in a vacuum oven. The filtrates are combined and weighed. About 10 g of filtrate is placed in a pre-weighed dish, air-dried to remove a substantial fraction of the solvent and then dried in a vacuum oven. Loss on drying and protein concentration are determined on both. About 70% of the protein is found in the extract. Results are shown in Table 9.

TABLE 9

Division of protein into extract and residue from corn gluten meal at approximately pH 6 and 65 wt % aqueous EtOH at 60° C.

|  | Solids (g) | Protein (g) | % of initial protein |
|---|---|---|---|
| Initial | 3.785 | 2.45 | |
| Extract | 2.03 | 1.71 | 69.8 |
| Residue | 1.89 | 0.74 | 30.2 |

Example 10

A 40 mg sample of the zein-depleted material matching the zein-enriched sample in Example 2 and derived from destarched corn gluten meal derived from Example 1 is weighed into a 2 mL microcentrifuge tube. A 60 mg sample of zein-depleted material matching the zein-depleted sample in Example 2 and derived from corn gluten meal from Example 1 was weighed into a 2 mL microcentrifuge tube. The intent is to equalize the ultimate protein concentrations loaded onto the gels. Two millimeters of absolute EtOH is added to each tube and mixed vigorously then placed at 55° C. for 2.5 hour to remove lipid materials. Solids and liquids are separated by centrifugation for 3 minutes at 13,000 g. The solvent is lifted off with a pipette. 2 mL of a 50:50 w/w mixture of EtOH:ethyl acetate is added to each tube and incubated for 30 minutes at 55° C. Solids and liquids are separated by centrifugation for 3 minutes at 13,000 g. The solvent is lifted off with a pipette. Samples are allowed to evaporate to dryness in a hood.

Figure 4:
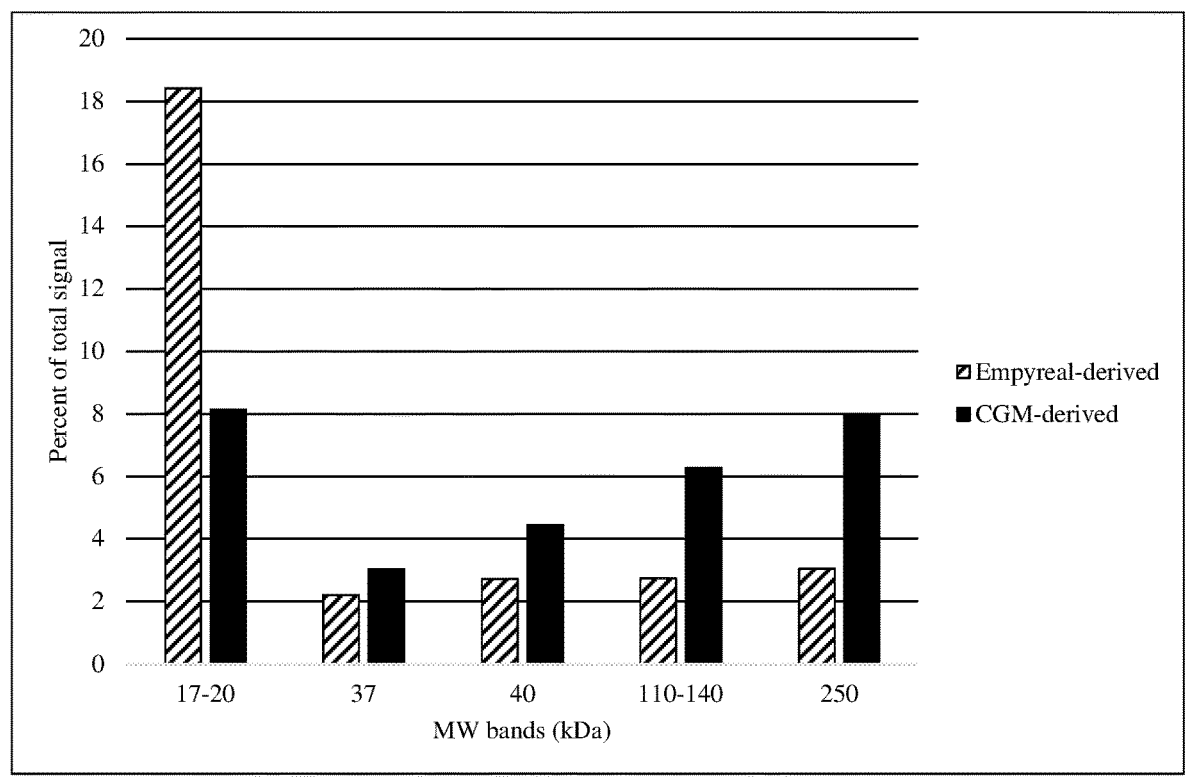
FIG. 4 illustrates quantitation of the five different molecular weight bands from residues of Empyreal and CGM after separation by SDS gel electrophoresis.

1000 microliters of 6M urea plus 100 microliters of 1N NaOH is added to each sample, mixed on a shaker for 1 hr at 1000 rpm and then left to incubate at room temperature to hydrate and dissolve. An aliquot containing 100 μL of Laemmli buffer containing 1 mM dithiothreitol is added to 100 μL of the alkaline-urea extract and exposed to a boiling water bath for 5 minutes. The sample is cooled and centrifuged at 13000 g for 5 minutes to remove particulates. A 20 μL aliquot is loaded into the wells of an AnykD™ Mini-PROTEAN® TGX™ Precast Gel and resolved on the Mini-PROTEAN® system. Gels are run until the marker dye reaches the bottom of the gel. Gels are stained with Bio-Safe™ Coomassie Brilliant Blue G-250 and destained in water. Destained gels are scanned and quantitated. The proportion of total signal associated with various MW bands is compared and demonstrated in Table 10 and FIG. 4.

TABLE 10

Percentage of total protein signal associated with select molecular weight bands after SDS gel electrophoresis of residue samples derived from Empyreal ® or corn gluten meal.

| Approx. MW (kDa) | Empyreal-derived | CGM-derived |
|---|---|---|
| 17-20 | 18.4 | 8.1 |
| 37 | 2.2 | 3.0 |
| 40 | 2.7 | 4.4 |
| 110-140 | 2.7 | 6.3 |
| 250 | 3.0 | 8.0 |

Example 11

To test the zein-depleted protein in the beef frank appli-cation, ingredients listed in Table 11 are weighed into disposable plastic containers and stored in the refrigerator until use. The control and the zein-depleted beef frank are prepared in duplicate by two analysts using a Cuisinart food processor with the blade attachment. One control and one sample frank is prepared by each analyst.

TABLE 11

|  | Formula/Inclusions | |
| Ingredients: | g | % |
| Ground Beef, 93% lean | 36.00 | 24.41 |
| Lard | 45.00 | 30.51 |
| Protein, LOD weight adjusted on 4 g | 4.00 | 2.71 |
| Salt | 4.50 | 3.05 |
| $1^{st}$ deionized water | 25.00 | 16.95 |
| $2^{nd}$ deionized water | 33.00 | 22.37 |
| Total | 147.50 | 100.00 |

The control is prepared by adding the ground beef, salt, water ($1^{st}$ and $2^{nd}$ deionized water are combined), and lard to the Cuisinart bowl. The mixer is quick-pulsed 5 times between each ingredient addition. After adding the lard, the mixer is quick-pulsed and then run at steady power for 1 minute. After the initial mix, the cover is removed and a rubber scraper used to scrape down the lid, bowl sides, and under the blade to ensure all ingredients are homogenized. The mixer is again run at steady power for 1 minute. 30 g of the mixture is weighed, in duplicate, into two tared 50 mL centrifuge tubes. The procedure is repeated by the second analyst using a clean/dry Cuisinart bowl for a total of 4 controls.

The zein-depleted beef frank is prepared by adding the protein to the $1^{st}$ deionized (25 g) water in a 50 mL centrifuge tube. The tube is hand shaken and set aside for initial equilibration. The beef and salt are added to a clean/dry Cuisinart bowl, quick-pulsing 5 times after each addi-tion. The water/protein suspension is poured into the bowl, and the tube is rinsed into the bowl using the $2^{nd}$ (35 g) water. The mixer is pulsed 5 times and the lard added. The rest of the procedure is the same as the control.

The centrifuge tubes containing the controls and zein-depleted samples are centrifuged at 3000 g for 1 minute to uniformly pack the mixture in the tube. Tubes are then placed in a water bath set to 75° C. for 35 minutes. Once removed from the water bath, the liquid is drained using a spatula to free the meat frank from the tube. The frank is removed entirely from the tube and rolled on a paper towel until the surface appeared dry. The frank is weighed to determine yield and losses. The addition of zein-depleted protein in a beef frank application increases the product yield 8.5% as compared to the control which contained no plant protein as demonstrated in Table 12.

TABLE 12

|  | Control | Zein-Depleted |
| % Yield | 68.3% | 73.4% |
|  | 67.7% | 73.1% |
|  | 68.7% | 73.4% |
|  | 67.5% | 75.4% |
| Average % Yield | 68.1% | 73.8% |
| % of Control | NA | 108.5% |

Example 12

The zein-depleted protein is included in a nutrition bar model application comparing to soy protein isolate (Supro 620 lot #M310014220). A mixture of 427 g Clearsweet 43/43 syrup, 150 g Isoclear 55, and 100 g glycerol is prepared and the syrup is warmed in a saucepan on an oven top burner to 50° C. with continuous stirring. 18.5 g of the syrup is then weighed in a beaker and 6.25 g protein ingredient (soy or corn) is added and mixed with a stiff metal spatula until homogenous. Final composition of the bar is 45% sugar, 25% plant protein, and 15% water. Four soy protein samples are prepared. Two particle sizes of zein-depleted samples, <105 μm and >105 μm, are prepared in duplicate.

The homogenized mixture is poured into a 1 oz sample cup, covered, and tapped on the bench to remove any air. Samples are stored in a sealed box and the resistance to compression is measured 24-72 hours after the protein addition using a texture analyzer. Zein-depleted protein produced a softer bar than soy protein isolate as demon-strated in Table 13.

TABLE 13

| Sample | Resistance to Compression (N) | Resistance to Compression (g-force) |
| Soy Protein Isolate-A | 22.0 | 2246 |
| Soy Protein Isolate-B | 16.3 | 1666 |
| Soy Protein Isolate-C | 21.4 | 2181 |
| Soy Protein Isolate-D | 23.5 | 2392 |
| Zein-Depleted <105 μm-A | 0.576 | 58.72 |
| Zein-Depleted <105 μm-B | 0.447 | 45.59 |
| Zein-Depleted >105 μm-A | 0.106 | 10.77 |
| Zein-Depleted >105 μm-B | 0.115 | 11.72 |

The invention claimed is:

1. A method of obtaining a corn protein zein-enriched fraction product and a corn protein zein-depleted fraction product, comprising obtaining an enzymatically destarched corn gluten meal that has been prepared by a process consisting of
    providing corn gluten meal,
    destarching the corn gluten meal by enzymatic treat-ment,
    optionally rinsing with water,
    optionally defatting using solvent or enzymes,
    optionally decolorizing by bleaching with enzymatic methods or chemical bleaching agents selected from ozone, persulfate and peroxides, and
    optionally filtering; and
carrying out an extraction step by treating the thus obtained enzymatically destarched corn gluten meal with an ethanol-water solvent comprising 55-80 wt % ethanol without an intervening step to obtain
    a) a corn protein zein-enriched fraction product com-prising 75 wt % to 95 wt % (dry solids) protein, and
    b) a corn protein zein-depleted fraction product com-prising 60 wt % to 80 wt % (dry solids) protein;
wherein
    the corn protein zein-enriched fraction product is enriched in aspartic acid, isoleucine and lysine as compared to a comparison corn protein zein-enriched fraction product that has been prepared from corn gluten meal that has not been enzymatically destarched, and the corn protein zein-enriched fraction product is depleted in glycine as compared to a comparison corn protein zein-enriched fraction product that has been prepared from corn gluten meal that has not been enzymatically destarched; and wherein the corn protein zein-depleted fraction product is enriched in leucine and tyrosine as compared to a comparison corn protein zein-enriched fraction product that has been prepared from corn gluten meal that has not been enzymatically destarched, and the corn protein zein-depleted fraction product is depleted in ammonium chloride, arginine, aspartic acid and lysine as compared to a comparison corn protein zein-enriched fraction product that has been prepared from corn gluten meal that has not been enzymatically destarched.

2. The method of claim 1, wherein the corn protein zein-depleted fraction product has less than 1.5% fat content.

3. The method of claim 1, wherein the corn protein zein-enriched fraction product has a protein yield of at least 50%.

4. The method of claim 1, wherein the corn protein zein-enriched fraction product has a protein yield of at least 30%.

5. The method of claim 1, wherein the corn protein zein-depleted fraction product is used in food applications.

6. The method of claim 1, wherein the corn protein zein-depleted fraction product comprises 15-20% of proteins having a molecular weight distribution profile ranging from 17-20 kDa.

7. The method of claim 1, comprising a defatting step subsequent to the extraction step.

8. The method of claim 1, comprising a defatting step prior to the extraction step.

9. The method of claim 1, wherein the corn protein zein-enriched fraction product comprises 78 wt % to 83 wt % (dry solids) protein and the corn protein zein-depleted fraction product comprises 70 wt % to 80 wt % (dry solids) protein.

10. The method of claim 1, wherein the corn protein zein-depleted fraction product comprises greater than 11.5% leucine, greater than 5.0% tyrosine, and less than 4.0% lysine on a protein basis.

11. The method of claim 1, wherein the corn protein zein-enriched fraction product has a protein yield of at least 55%.

12. The method of claim 1, wherein the corn protein zein-enriched fraction product has a protein yield of at least 40%.

13. The corn protein zein-enriched fraction product made by the process of claim 1.

14. The corn protein zein-depleted fraction product made by the process of claim 1.

15. A food product comprising the corn protein zein-depleted fraction product of claim 14.

* * * * *